United States Patent [19]

Herd

[11] Patent Number: 5,107,025
[45] Date of Patent: Apr. 21, 1992

[54] PROCESS FOR THE PREPARATION OF [5-AMINO-2-(2-HYDROXYETHYLAMINO)-PHENYL](2-HYDROXYETHYL) SULPHONE

[75] Inventor: Karl-Josef Herd, Odenthal-Holz, Fed. Rep. of Germany

[73] Assignee: Bayer Aktiengesellschaft, Leverkusen, Fed. Rep. of Germany

[21] Appl. No.: 603,097

[22] Filed: Oct. 25, 1990

[30] Foreign Application Priority Data

Dec. 2, 1989 [DE] Fed. Rep. of Germany ........ 3939966

[51] Int. Cl.$^5$ ........................................... C07C 315/02
[52] U.S. Cl. ................................................. 564/440
[58] Field of Search ........................................ 564/440

[56] References Cited

U.S. PATENT DOCUMENTS 4,577,015 3/1986 Jager et al. .............................. 544/76
4,992,589 2/1991 Fuchs et al. ........................ 564/440

OTHER PUBLICATIONS

March, Advanced Organic Chemistry, Third Ed., pp. 1109–1110, (1978).

Primary Examiner—Mary C. Lee
Assistant Examiner—M. S. H. Gabilan
Attorney, Agent, or Firm—Sprung Horn Kramer & Woods

[57] ABSTRACT

A process for the preparation of the sulphone of the formula:

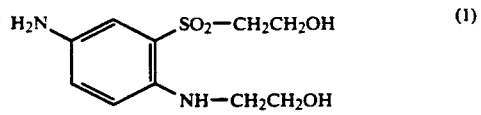

(1)

consists in reductive cleavage of azo/azoxy dyestuffs of the formula

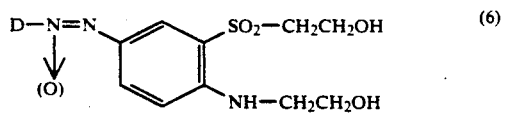

(6)

The invention also relates to the azo/azoxy dyestuffs mentioned.

2 Claims, No Drawings

PROCESS FOR THE PREPARATION OF [5-AMINO-2-(2-HYDROXYETHYLAMINO)-PHENYL](2-HYDROXYETHYL) SULPHONE

The invention relates to a process for the preparation of [5-amino-2-(2-hydroxyethylamino)phenyl] (2-hydroxyethyl) sulphone of the formula

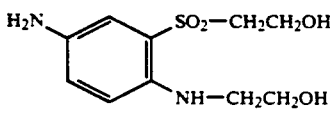

characterized in that benzothiazoles of the formula

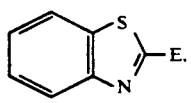

in which E is H or $CH_3$, are reacted with ethylene oxide is an aqueous reaction medium to give N-formyl- or N-acetyl-N-(2-hydroxyethyl)aniline derivatives of the formula

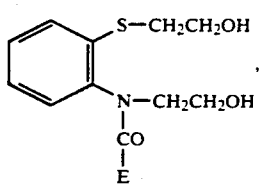

which are then hydrolyzed to give the aniline derivative of the formula

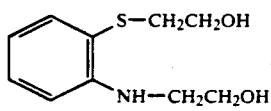

which is then coupled onto a diazotized amine $D-NH_2$ to give monoazo dyestuffs of the formula

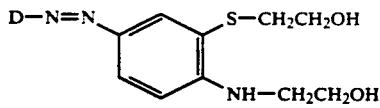

the azo dyestuffs (5) are then oxidized to the azo/azoxy dyestuffs of the formula

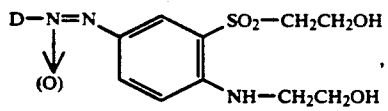

which are then cleaved reductively in a manner known per se to give $D-NH_2$ and (1).

The invention also relates to the new azo and azo/azoxy dyestuffs of the formulae (5) and (6).

D represents the radical of a diazo component, in particular from the benzene, naphthalene or hetaryl series.

D can be substituted by customary substituents, for example Cl, Br, F, $C_1-C_4$-alkyl, $C_1-C_4$-alkoxy, carbalkoxy, carboxyl, amino, alkylamino, dialkylamino, sulphonamido, alkylsulphonyl and in particular sulpho. Preferably, those substituents which do not undergo any change during the oxidation and reduction are suitable. The alkyl groups can contain customary substituents.

Those azo and azo/azoxy dyestuffs of the formulae (5) and (6) are preferred in which the radical D is selected in such a manner that after the reduction of (6) to $D-NH_2$ and (1) the diazo component $D-NH_2$ can be easily separated off and again be used in the synthetic sequence. Examples of these types of radicals D are

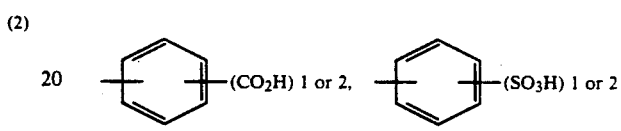

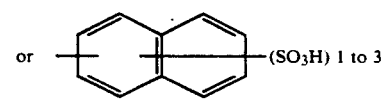

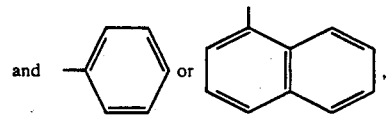

it being possible for the benzene and naphthalene rings to contain further substituents, for example Cl, Br, $C_1-C_4$-alkyl, $C_1-C_4$-alkoxy or carboxyl.

Sulpho-containing or carboxyl-containing diazo components have the advantage that the oxidation and the reduction can be carried out in an aqueous reaction medium.

Azo and azo/azoxy dyestuffs of the formulae

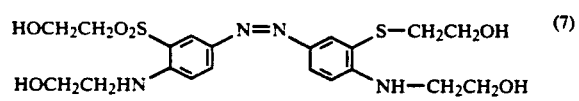

and

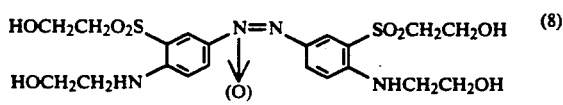

are preferred, since the reduction of (8) uniformly only yields (1). (7) can be prepared by diazotization of (1) and coupling onto (4).

The reaction of the benzothiazoles (2) with excess ethylene oxide is preferably carried out in water at temperatures between 20° and 120° C., preferably between 40° and 90° C., and in an autoclave under a pressure of 0.2 to 2.0 bar. The ethylene oxide is metered in at such a rate that a pH of 8 to 12, preferably 9.0 to 10.5, is reached. During this reaction, the benzothiazole probably passes through the intermediate stages

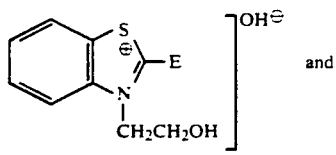

and

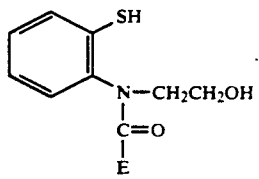

Thus, by simple addition of ethylene oxide, aqueous solutions of 2-(2-hydroxyethylmercapto)-N-acyl-N-(2-hydroxyethyl)aniline of the formula (3) are surprisingly obtained directly from the benzothiazoles (2).

The ethoxylation reaction can also be carried out in a reaction medium composed of water and a water-miscible organic solvent. Additions of emulsifiers or phase-transfer catalysts can accelerate the reaction. In principle, the reaction solutions can be directly further reacted.

The N-formyl- and N-acetylaniline derivative of the formula (3) can be hydrolysed not only under acidic but also under alkaline reaction conditions at temperatures of 80° to 120° C., if appropriate under pressure. The free aniline base of the formula (4) separates at pH values above 7, i.e. under alkaline conditions, in the form of an oil phase.

The coupling of (4) onto diazotized amines D—NH$_2$ to give dyestuffs of the formula (5) is most advantageously carried out at 0° to 30° C. in a pH range of 1.0 to 5.0 in an aqueous medium. Here, too, the use of emulsifiers or coupling accelerators, such as, for example, urea, can prove advantageous. The dyestuffs (5) are in most cases obtained in the form of crystalline compounds or can be salted out as such. Since the coupling reactions proceed in most cases relatively uniformly, the intermediate (5) can often be oxidized directly without isolation to give azo/azoxy dyestuffs of the formula (6). In this step, the use of hydrogen peroxide in the presence of catalytic amounts of tungstates has proved advantageous. The oxidation is carried out in aqueous medium at 20° to 100° C., preferably at 40° to 80° C. and pH values of 6 to 8. The oxidation passes through the corresponding sulphoxide compounds of the formula

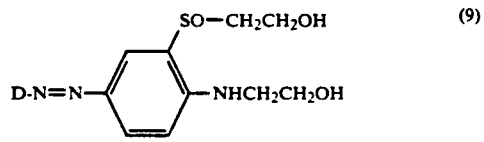

as intermediates, which can be monitored by chromatography. Further suitable oxidizing agents are, for example, also perborates, persulphates, or persulphonic acids.

The azo/azoxy dyestuffs of the formula (6) can be isolated as yellow to red, crystalline, water-soluble compounds. Upon protonation, their solutions show a distinct bathochromic shift. In most dyestuffs (6), the azo content predominates; as a rule, the azoxy content is limited to 5%, such as, for example, in (8). The azo dyestuff (8a) can be obtained relatively uniformly by recrystallization from water or alcohol.

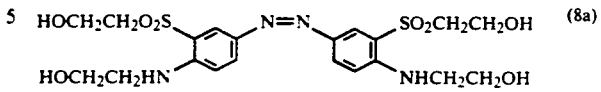

The reduction of (6) or (8) or (8a) to (1) and D—NH$_2$ can be carried out by methods such as described by R. Schröter in Handbuch für präparative Methoden der organischen Chemie (Handbook of preparative methods in organic chemistry), Houben-Weyl, Volume XI, Part 1, pages 522 to 531. According to this handbook, reduction using sodium dithionite or glucose or, alternatively, catalytic reduction using hydrogen is suitable. Suitable catalysts are primarily Raney nickel, palladium/carbon or platinum compounds. The reductions are preferably carried out in water, water/alcohol mixtures or alcohols at 20° to 80° C.

In the case of (8) and (8a), a uniform solution of (1) is obtained. (1) can be directly further reacted in this form, for example it can be condensed with chloranil or, alternatively, diazotized or isolated as a crystalline substance by concentrating the solution.

In all other cases, the reduction leads to a solution or suspension of (1) and D—NH$_2$. The latter should therefore be already selected as a diazo component in such a manner that it can be separated from (1) almost quantitatively. Therefore, it is advantageous to use aminocarboxylic acids or aminosulphonic acids as diazo components, such as, for example 2-aminobenzoic acid
4-aminobenzoic acid
2-aminobenzenesulphonic acid
3-aminobenzenesulphonic acid
4-aminobenzenesulphonic acid
2-amino-4-methylbenzenesulphonic acid
6-amino-2-naphthalenesulphonic acid
7-amino-1,3-naphthalenedisulphonic acid
2-amino-1,5-naphthalenedisulphonic acid
4-amino-1-naphthalenesulphonic acid
5-amino-1-naphthalenesulphonic acid etc.

If the reductions are carried out in a purely aqueous medium, the result in these cases is mostly solutions from which the benzoic acids or aminosulphonic acids can be precipitated as betaines and separated off by acidification and, if necessary, salting out. (1) remains in the acidic aqueous solution and can be isolated or further reacted, as already described.

If aniline or α-naphthylamine is selected as possible diazo component, after the reduction it must be separated off from (1) by means of steam distillation. Other aniline derivaties which are volatile in steam are also suitable as diazo components.

Compound (1) is used, for example, for the preparation of interesting azo dyestuffs, such as Example 17 from DOS (German Published Specification) 3,512,340

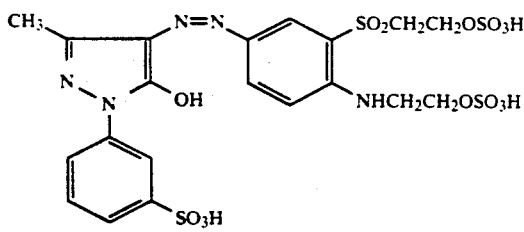

or Example 5 from EP 279,351

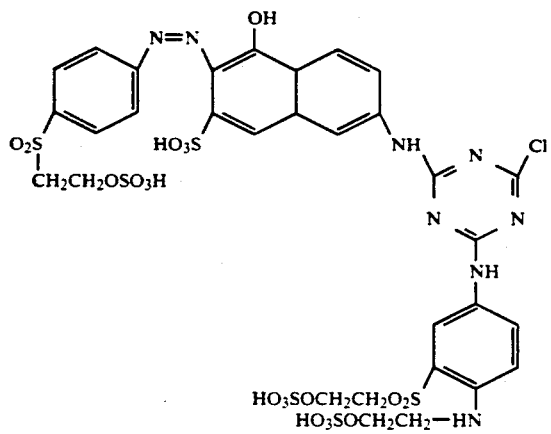

and for the preparation of triphendioxazine dyestuffs, such as Example 1 from EP 153,599

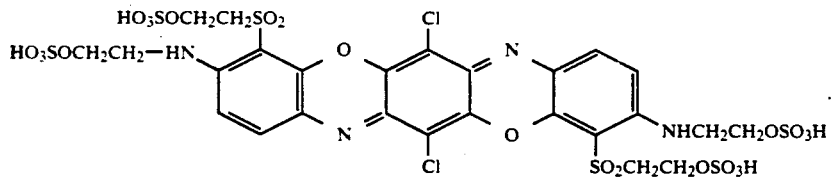

Azo dyestuffs of the formula (5) and (6) are used for the colouring of paper and the dyeing of wool, synthetic polyamide fibres or leather. Clear, brilliant yellow colorations or dyes are obtained.

The formula given for sulpho-containing and carboxyl-containing azo dyestuffs are those of the free acids. The preparation in general gives the salts, in particular the alkali metal salts, such as sodium salts, potassium salts or lithium salts.

EXAMPLE 1

An emulsion of 135 g of benzothiazole and 1 g of a conventional emulsifier in 500 ml of water is heated to 60° C., and nitrogen is passed through it for 1 hour. A total of about 300 g of ethylene oxide is then metered in over a period of about 12 hours at such a rate that a pH between 9.5 and 10.5 is maintained. The reaction is monitored by thin-layer chromatography. As soon as less than 1% of the starting concentration of the benzothiazole can be detected, the ethylene oxide addition is stopped, and the reaction solution is heated at 80° C. for a further 2 hours, while passing a vigorous nitrogen stream through it. After the remaining ethylene oxide has been removed in this manner, the reaction solution of about 800 ml is cooled to room temperature. In addition to glycol and small amounts of polyglycols, the reaction solution contains a relatively uniform hydroxyethylaniline derivative of the formula

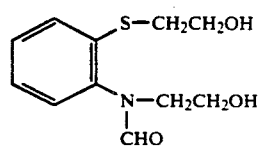

and can be directly further reacted.

The characterize the product, an 80 ml sample of the solution is worked up at pH 7 by extraction and distillation. A viscous colourless oil is obtained, to which the above structure can be assigned on the basis of the $^1$H-NMR and IR data.

| | |
|---|---|
| IR (Nujol paste): | 1662 cm$^{-1}$ (CO vibr.) |
| 1H-NMR (d$_6$-DMSO): δ = | 3.05(2H, m); 3.48(2H, m); 3.60(2H, m); 3.65(2H, m); 4.68(t, OH); 4.94(t, OH); 7.15–7.50(m, 4H); 8.00 (s, CHO). |
| Mass spectrum: m/e = | 241(M+, 45%), 213(M+ -CO, 45%); 182(65%); 164 (55%); 136(100%). |

EXAMPLE 2

200 ml of a 70% strength sulphuric acid are added to 800 ml of the reaction solution from Example 1, and the mixture is heated at 90°–95° C. for 1 hour. It is then cooled, neutralized with concentrated sodium hydroxide solution and outside cooling and then brought to a pH of 12.5, as a result of which a colourless oil separates.

(However, it is also possible to hydrolyze the reaction solution from Example 1 under alkaline conditions by bringing it to a pH of 12.5–13.0 with sodium hydroxide solution and heating it at 80°–85° C. for 30 minutes)

The oil is separated off and characterized as the hydroxyethylaniline of the formula

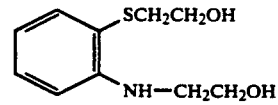

$^1$H-NMR(d$_6$-DMSO): δ = 2.77(t, 2H); 3.18(m, 2H); 3.42(m, 2H); 3.60(m, 2H); 4.81(t, OH); 4.83(t, OH); 5.46(t, NH); 6.50–6.63 (m, 2H); 7.15(m, 1H); 7.30 (m, 1H).

EXAMPLE 3

An emulsion of 149 g of 2-methylbenzothiazole, 1 g of a conventional emulsifier and 500 ml of water is heated in a pressurized container to 60° C., and nitrogen is passed through it for 1 hour. The autoclave is then sealed and heated to 80° C. About 250 g of ethylene oxide are then injected over a period of 3 to 4 hours in such a manner that an internal pressure of 1.5 bar and a pH between 9.5 and 10.5 are maintained. After the total amount of ethylene oxide has been added, heating at 80° C. is continued until the pressure has dropped to 0.1/–0.2 bar. The pressure is released, and the remaining ethylene oxide is removed by passing a vigorous nitrogen stream through the mixture at 80° C. The reaction solution of about 750 ml is cooled to 20° C. 50 ml of this colourless solution are concentrated on a rotary evaporator, and the remaining oil is purified by column chromatography, i.e. glycol and polyglycols are separated off. A colourless viscous oil is isolated, which is identified by spectroscopy as the compound of the formula

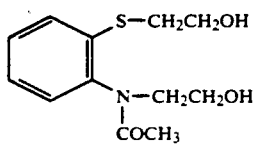

$^1$H-NMR(d$_6$-DMSO): δ = 1.65(s, COCH$_3$); 3.04(dt, 1H); 3.12(t, 2H); 3.50(dt, 2H); 3.63(t, 2H); 4.08(dt, 1H); 4.60(broad, 2 OH); 7.17–7.50(m, 4H).
IR(Nujol): 1640 cm$^{-1}$ (CO vibration)

Acid or alkaline hydrolysis of these N-acetylaniline compounds produces, in analogy to Example 2, the free base 2-(2-hydroxyethylmercapto)-N-(2-hydroxyethyl)-aniline.

EXAMPLE 4

23.6 g of the monosodium salt of 7-amino-1,3-naphthalenedisulphonic acid are stirred in 150 ml of water/50 g of ice and 20 ml of concentrated hydrochloric acid, and 17 ml of a sodium nitrite solution (300 g/l) are added dropwise at 5 to 10° C. The diazotization is completed after 1.5 hours. The small excess of nitrite is destroyed by adding sulphamic acid. The cream-coloured suspension is brought to a pH of 2.5 with sodium carbonate solution. A solution of 15.0 g of the free base from Example 2 in 100 ml of water adjusted to a pH of 2.0 is added dropwise at about 10° C. The mixture is stirred at 10° C. (pH 1.5–2.0) for 4 to 5 hours. To complete the coupling reaction, the pH is increased to 4.5 by adding sodium acetate, and the mixture is stirred again for 2 hours. 40 g of common salt are added, the mixture is stirred for 1 hour, and the precipitate is isolated by filtering it off with suction. It is dried to give 48 g of a salt-containing dyestuff of the formula

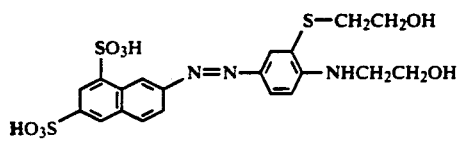

λmax = 454 nm (H$_2$O, pH 7-8)

$^1$H-NMR(d$_6$-DMSO): δ = 2.88(t, 2H); 3.35(t, 2H); 3.50(t, 2H); 3.65(m, 2H); 5.15(broad s, 2 OH); 6.17 (t, NH); 6.85(d, 1H); 7.83–8.07(m, 4H); 8.16(s, 1H); 8.30(s, 1H); 9.30(s, 1H).

EXAMPLE 5

47 g of the dyestuff from Example 4 are stirred in 250 ml of water at a pH of 8-8.5, 0.2 g of sodium tungstate is added, and the mixture is heated to 70° C. 30 ml of an approximately 35% strength aqueous hydrogen peroxide solution are added dropwise. During this addition, the temperature should be between 70° and 80° C. After about 2 hours, the oxidation is checked by thin-layer chromatography. The sulphoxide derivative which is an intermediate in the oxidation can also be detected. If necessary, another 10 to 15 ml of hydrogen peroxide solution are added to also oxidize the remaining sulphoxide derivative to the sulphone derivative. The mixture is then stirred at 80° C. for 2 hours, cooled to room temperature and acidified with sulphuric acid to a pH of 0.5 to 1.0. The dyestuff is salted out with 35 g of common salt and 5 g of potassium chloride and isolated. After drying, 38 g of a salt-containing dyestuff of the formula

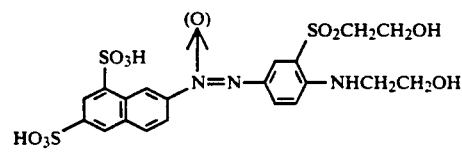

are obtained. On the basis of TLC and NMR, the azoxy content seems to be no more than a few per cent.

| λmax - 406 nm (H$_2$O, pH 7-8) $^1$H-NMR (d$_6$-DMSO): δ = | 3.42(t, 2H); 3.55(t, 2H); 3.68(t, 2H); 3.75(t, 2H); 5.0–5.3(broad, 2 OH); 6.9 (broad s, NH); 7.13(d, 1H); 7.98(dd, 1H); 8.05–8.17(m, 2H); 8.20(s, 1H); 8.27(d, 1H); 8.32(d, 1H); 9.35(d, 1H). |
|---|---|

In analogy to the coupling procedure (Example 4) and oxidation procedure (Example 5), if the diazo component in Example 4 is varied, it is possible to prepare further interesting dyestuffs having azosulphide and azo/azoxysulphone structure:

| Ex. | D | λmax (H$_2$O, pH 7-8) |
|---|---|---|
| | (structure with S—CH$_2$CH$_2$OH, NHCH$_2$CH$_2$OH, D-N=N-phenyl) | |
| | HO$_2$C—phenyl | 432 nm |

-continued

| Ex. | D | λmax (H₂O, pH 7-8) |
|---|---|---|
| 7 | [structure: phenyl with CO₂H] | 406 nm |
| 8 | [structure: phenyl with SO₃H] | 414 nm |
| 9 | [structure: naphthyl with HO₃S] | 448 nm |
| 10 | [structure: benzothiazole with SO₃H, CH₃ and phenyl] | 410, 470 (sh)nm |

[structure: D—N=N(→O)—phenyl with SO₂CH₂CH₂OH and NHCH₂CH₂OH]

| 11 | | 396 nm |
| 12 | | 374 nm |
| 13 | | 397 nm |
| 14 | | 402, 455 (sh)nm |
| 15 | | 406, 470 (sh)nm |

EXAMPLE 16

12.5 g of 4-aminobenzenesulphonic acid are diazotized analogously to Example 4, and the resulting suspension is brought to a pH of 2.5 with sodium carbonate solution. A solution of 15.0 g of the free base from Example 2 in 100 ml of water adjusted to a pH of 2.0 is added dropwise to the suspension at 5° to 10° C. This mixture is stirred at a pH of 1.5 to 2.5 at 10° C. for 5 hours and then at pH 3.5 to 4.0 at 10° C. for 3 hours. During this procedure, the pH is increased with sodium acetate solution. After the coupling is completed, the pH is adjusted to 8.0 with sodium carbonate solution. A clear solution of the azo dyestuff of the formula

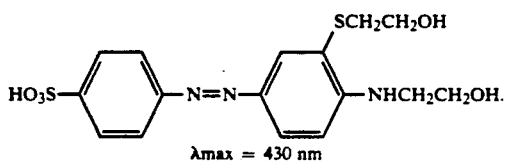

$\lambda max = 430$ nm is obtained. 0.2 g of sodium tungstate is added to the solution, and the mixture is heated to 60° C. 35 ml of a 35% strength aqueous hydrogen peroxide solution are metered in over a period of 15 minutes, and the reaction is kept at 70° to 80° C. The oxidation to the sulphone is completed after about 3 to 4 hours. The mixture is cooled to 20° C., brought to a pH of 6.0, and the product is salted out with 45 g of common salt. After stirring for another 2 hours, it is filtered off with suction and dried to give 32 g of a golden-yellow dyestuff powder of the structure

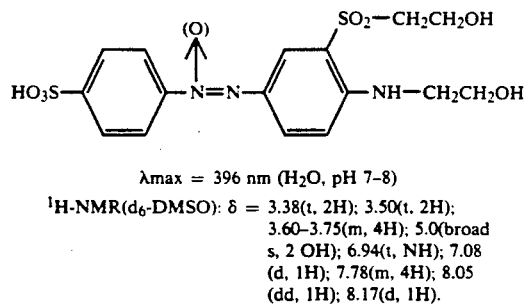

$\lambda max = 396$ nm (H₂O, pH 7-8)

¹H-NMR(d₆-DMSO): δ = 3.38(t, 2H); 3.50(t, 2H); 3.60–3.75(m, 4H); 5.0(broad s, 2 OH); 6.94(t, NH); 7.08 (d, 1H); 7.78(m, 4H); 8.05 (dd, 1H); 8.17(d, 1H).

EXAMPLE 17

A) 35 g of the dyestuff from Example 5 are dissolved in 150 ml of water at a pH of 7, 0.2 g of Raney-Nickel catalyst is added, and the dyestuff is reduced in an autoclave with the 2.5-fold equimolar amount of hydrogen. During this reaction, the batch is allowed to warm to 40° to 50° C. After the catalyst has been separated off, a clear, pale brownish solution is obtained, from which the 7-amino-1,3-napthalenedisulphonic acid can be precipitated in the form of the monosodium salt after acidification to a pH of 1.0, salting out with 10 g of common salt and cooling to 15° C. The desired [5-amino-2-(2-hydroxyethylamino)phenyl] (2-hydroxyethyl) sulphone of the formula

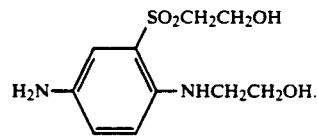

remains in solution. The solution can now been directly further reacted, for example after neutralization, for example with chloranil, such as described in EP 153,599. However, it can also be concentrated to dryness on a rotary evaporator after neutralization. A salt-containing product is then obtained, which can be purified by recrystallization from water or alcohol and then melts at 130° C.

B) The same product or the same solution is also obtained by reacting 20 g of the dyestuff from Example 16 in 100 ml of water at pH 7-8 and 50° C. with 15.5 g of sodium dithionite over a period of 10 minutes. The initially golden-yellow solution is decolorized. It is cooled to 20° C. and brought to a pH of 1.5 with hydrochloric acid. After addition of 20 g of common salt, it is stirred for 4 to 5 hours until the 4-aminobenzenesulphonic acid has completely precipitated. Filtration gives a solution of relatively uniform [5-amino-2-(2-hydroxyethylamino)phenyl] (2-hydroxyethyl) sulphone.

This important intermediate is also obtained by catalytic hydrogenation analogously to Example 17 A of the azo/azoxy dyestuffs of Examples 11 to 16 and separation of the diazo component D—NH₂ likewise formed, as described.

EXAMPLE 18

18.8 g of [5-amino-2-(2-hydroxyethylamino)phenyl] (2-hydroxyethyl) sulphone are dissolved in 150 ml of water, 50 g of ice and 25 ml of hydrochloric acid are diazotized at 0° to 3° C. with 17 ml of a sodium nitrite solution (300 g/l). The diazotization is completed after 30 minutes; it results in a solution.

15.2 g of the free base from Example 2 are suspended in 50 ml of water and dissolved by the addition of 25 ml of acetic acid. This solution is added to the completely diazotized solution, and the pH is increased to 3.5 to 4.0 by adding sodium acetate solution. The reaction temperature is maintained at 0°-5° C. with ice, and the mixture is stirred at a pH of 3.5 to 4.0 for 8 hours. A crystalline yellow precipitate is formed, which is filtered off with suction, washed with 50 ml of water and dried. 31.5 g of the azo dyestuff of the formula

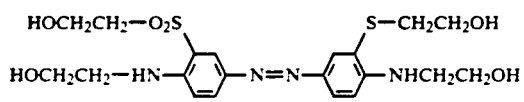

are obtained, which can be recrystallized from water or alcohol and melts at 177°-178° C.

| | |
|---|---|
| $\lambda_{max}$ - 458 nm (H₂O, pH 7-8) | 2.87(t, 2H); 3.35(m, 4H); |
| $^1$H-NMR (d₆-DMSO): δ = | 3.50(m, 4H); 3.60-3.75(m, 6H); 4.95(broad s, 4 OH); 6.13(t, NH); 6.77(t, NH); 6.80(d, 1H); 7.05(d, 1H); 7.75(dd, 1H); 7.90(d, 1H); 7.95(dd, 1H); 8.07(d, 1H). |

EXAMPLE 19

30 g of the azo dyestuff from Example 18 are suspended in 150 ml of water, the mixture is brought to a pH of 8 and, after the addition of 0.2 g of sodium tungstate, heated to 60° C. (however, it is also possible to use the coupling mixture from Example 18 directly instead of the isolated dyestuff). 30 ml of a 35% strength hydrogen peroxide solution are slowly added dropwise. The reaction is weakly exothermic. A clear orange-red solution is obtained at 75° C. It is stirred at 75° to 80° C. for another hour and then cooled to room temperature. This results in the crystallization of the azo dyestuff in golden-yellow crystals. To complete the precipitation, 10 g of potassium chloride are added, and the mixture is cooled to 0° C. The product is filtered off with suction, washed with a small amount of water and dried at 60° C. in vacuo to give 28.2 g of the azo dyestuff of the formula

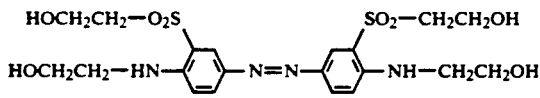

which can be recrystallized from water or alcohol and has a melting point of 200° C.

| | |
|---|---|
| $\lambda_{max}$ - 442 nm (H₂O, pH 7-8) | 3.38(t, 4H); 3.50(t, 4H); |
| $^1$H-NMR (d₆-DMSO): δ = | 3.62-3.75(m, 8H); 4.93(t, 2 OH); 4.97(t, 2 OH); 6.95 (t, 2 NH); 7.06(d, 2H); 8.01 (dd, 2H); 8.12(d, 2H). |

EXAMPLE 20

25.8 g of the azo dyestuff from Example 19 are suspended in 200 ml of water, 0.2 g of Raney-Nickel catalyst is added, and the dyestuff is hydrogenated in an autoclave with a 2-fold equimolar amount of hydrogen. The reaction is weakly exothermic; a temperature of 35° to 40° C. is reached. A colourless reaction solution is obtained, if the catalyst is separated off at 40° C. by filtration. Concentration of the solution on a rotary evaporator gives 26 g of uniform crystalline [5-amino-2-(2 2-hydroxyethylamino)phenyl] (2-hydroxyethyl) sulphone of the formula

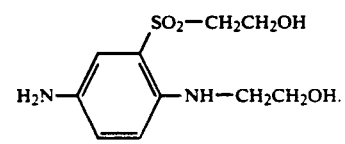

EXAMPLE 21

If diazotized aniline is coupled analogously to Example 16 in aqueous medium onto the free base 2-(2-hydroxyethylmercapto)-N-(2-hydroxyethyl)aniline, and the azo compound obtained is oxidized at 60°-80° C. with hydrogen peroxide solution, a crystalline azosulphone of the formula

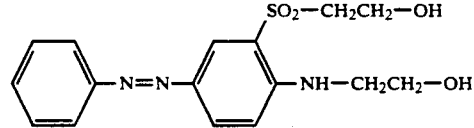

is obtained. The golden-yellow compound ($\lambda_{max}$=392 nm (H₂O, pH 7-8) melts at 126° C.

| | |
|---|---|
| $^1$H-NMR (d₆-DMSO): δ = | 3.38(m, 2H); 3.50(m, 2H); 3.68(m, 2H); 3.73(m, 2H); 4.90(t, OH), 4.95(t, OH); 6.92(t, NH); 7.08(d, 1H); 7.45-7.58(m, 3H); 7.80(d, 1H); 7.86(d, 1H); 8.04(dd, 1H); 8.18(d, 1H). |

EXAMPLE 22

20 g of the azo dyestuff from Example 21 are suspended in 200 ml of water, 0.2 g of Raney nickel catalyst is added, and the dyestuff is hydrogenated in an autoclave with a 2-fold equimolar amount of hydrogen. A temperature of 40° C. is reached during this process. After the reaction is finished, the catalyst is separated off, and the aniline formed is removed completely from the solution by steam distillation. The remaining solution which contains [5-amino-2-(2-hydroxyethylamino)-phenyl] (2-hydroxyethyl) sulphone can be used directly for further reactions, such as, for example, the condensation with chloranil (cf. Example 17). The above reduction can also be carried out, for example, in methanol or in a methanol-water mixture.

I claim:
1. Process for the preparation of [5-amino-2-(2-hydroxyethylamino)phenyl] (2-hydroxyethyl) sulphone of the formula

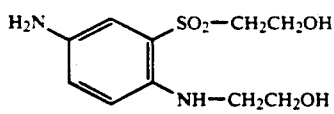 (1)

characterized in that benzothiazoles of the formula

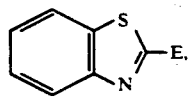 (2)

in which

E is H or $CH_3$, are reacted with ethylene oxide in an aqueous reaction medium to give N-formyl- or N-acetyl-N-(2-hydroxyethyl)aniline derivatives of the formula

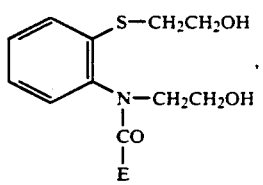 (3)

which are then hydrolysed to give the aniline derivative of the formula

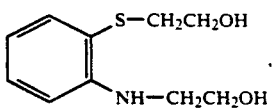 (4)

which is then coupled onto a diazotized amine $D-NH_2$ to give monoazo dyestuffs of the formula

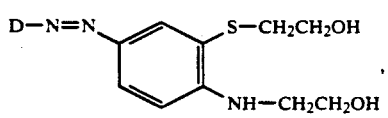 (5)

the azo dyestuffs (5) are then oxidized to give azo/azoxy dyestuffs of the formula

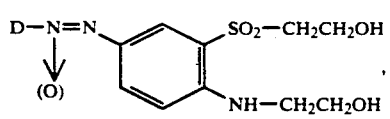 (6)

which are then cleaved reductively in a manner known per se to give $D-NH_2$ and (1), in which D is the radical of a diazo component.

2. Process according to claim 1, characterized in that amines $D-NH_2$ are used which contain sulpho and/or carboxyl groups or $D-NH_2$ represents aniline or a-naphthylamine.

* * * * *